United States Patent [19]

Temsamani et al.

[11] Patent Number: 5,558,992
[45] Date of Patent: Sep. 24, 1996

[54] DETECTION OF SYNTHETIC OLIGONUCLEOTIDES EXTRACTED FROM BODY FLUIDS OR TISSUES

[75] Inventors: Jamal Temsamani; Sudhir Agrawal, both of Shrewsbury, Mass.

[73] Assignee: Hybridon, Inc., Worcester, Mass.

[21] Appl. No.: 241,062

[22] Filed: May 11, 1994

Related U.S. Application Data

[63] Continuation of Ser. No. 2,786, Jan. 8, 1993, abandoned.

[51] Int. Cl.$^6$ ...................................................... C12Q 1/68
[52] U.S. Cl. ............................................................. 435/6
[58] Field of Search .................................. 435/6; 514/44

[56] References Cited

U.S. PATENT DOCUMENTS 4,483,920  11/1984  Gillespie et al. ........................... 435/6

FOREIGN PATENT DOCUMENTS

WO8808036  10/1988  WIPO.
WO9200983  1/1992  WIPO.
WO9218649  10/1992  WIPO.

OTHER PUBLICATIONS

Hanes et al, Nucleic Acid Hybridization, CRL Prevs, 1985, pp. 176–177.
Stein et al, Science, v. 261, Aug. 20, 1993 pp. 1004–1012.
Agrawal et al., Proc. Natl. Acad. Sci. USA 88, 7595–7599 (1991).

*Primary Examiner*—George C. Elliott
*Attorney, Agent, or Firm*—Banner & Allegretti, Ltd.

[57] ABSTRACT

The invention provides a method for detecting specific synthetic oligonucleotides that are present in body fluid or tissue samples taken from an animal or human patient to whom oligonucleotides have been administered.

4 Claims, 2 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i i ) HYPOTHETICAL: NO ( i v ) ANTI-SENSE: NO ( x i ) SEQUENCE DESCRIPTION: SEQ ID NO:1:

CTCTCGCACC CATCTCTCTC CTTCT 25

( 2 ) INFORMATION FOR SEQ ID NO:2:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i i ) HYPOTHETICAL: NO ( i v ) ANTI-SENSE: YES ( x i ) SEQUENCE DESCRIPTION: SEQ ID NO:2:

GAGAGATGGG TGCGAGAG 18

DETECTION OF SYNTHETIC OLIGONUCLEOTIDES EXTRACTED FROM BODY FLUIDS OR TISSUES

This application is a continuation of application Ser. No. 08/002,786, filed Jan. 8, 1993, now abandoned.

BACKGROUND OF THE INVENTION

1. Field of the Invention

The invention relates to the detection of specific nucleic acid sequences. More particularly, the invention relates to the detection of synthetic oligonucleotides present in body fluids or tissues.

2. Summary of the Related Art

Detection of specific nucleic acid sequences present in cells is generally known in the art. Southern, J,. Mol. Biol. 98:503–517 (1975) teaches detection of specific sequences among DNA fragments separated by gel electrophoresis, using "blotting" or transfer of the DNA fragments to a membrane, followed by hybridization of denatured DNA fragments with a radioactive probe and autoradiography. This procedure has also been extended to the detection of RNA molecules extracted from cells or tissues. More recently, faster and quantitative "dot-blotting" procedures have been developed for rapid detection of DNA or RNA from tissues or cells.

Recently, considerable interest has been generated in the development of synthetic oligonucleotides as therapeutic or gene expression modulating agents in the so-called antisense approach. For example, Agrawal, Trends in Biotechnology 10:152–158 (1991) extensively reviews the development of antisense therapeutic approaches. For an antisense therapeutic approach to be effective, oligonucleotides must be introduced into a patient and must reach the specific tissues to be treated. Consequently, there is a need to be able to detect oligonucleotides in body fluids or tissues. In animal models, radiolabelled oligonucleotides have been administered to the animal and their distribution within body fluids and tissues has been assessed by extraction of the oligonucleotides followed by autoradiography (See Agrawal, Temsamani and Tang, Proc. Natl. Acad. Sci. 88:7595–7599 (1991). As a practical matter, however, these methods cannot be extended to human patients. Unfortunately, the various techniques for detecting specific unlabelled nucleic acid sequences present in body fluids or tissues has only been extended to polynucleotides, such as large DNA or RNA molecules. Due to the small size of oligonucleotides, special problems relating to nonspecific binding or background, as well as to absence of binding, nondetection or false negatives exist. Thus, there remains a need to develop procedures for the detection of specific synthetic oligonucleotide sequences present in body fluids and tissues.

BRIEF SUMMARY OF THE INVENTION

The invention provides a method for detecting the presence of synthetic oligonucleotides in body fluids or tissue samples taken from a laboratory animal or a human patient. In the method according to the invention, body fluid or tissue samples are taken from an animal or human to whom an oligonucleotide has been administered and are proteolytically digested, then extracted. Total nucleic acids are then precipitated from the extracted samples and are transferred to a hybridization membrane. The hybridization membrane with attached nucleic acids is prehybridized, then hybridized with a labelled oligonucleotide that is complementary to the oligonucleotide that was administered to the animal or patient. Presence of hybridized, labelled oligonucleotide is then detected by standard procedures. The method according to the invention is useful both for detection and localization of oligonucleotides in patients undergoing antisense oligonucleotide therapy and in animal models used in studies for pharmacokinetic properties of oligonucleotides.

DETAILED DESCRIPTION OF THE PREFERRED EMBODIMENTS

Figure 1:
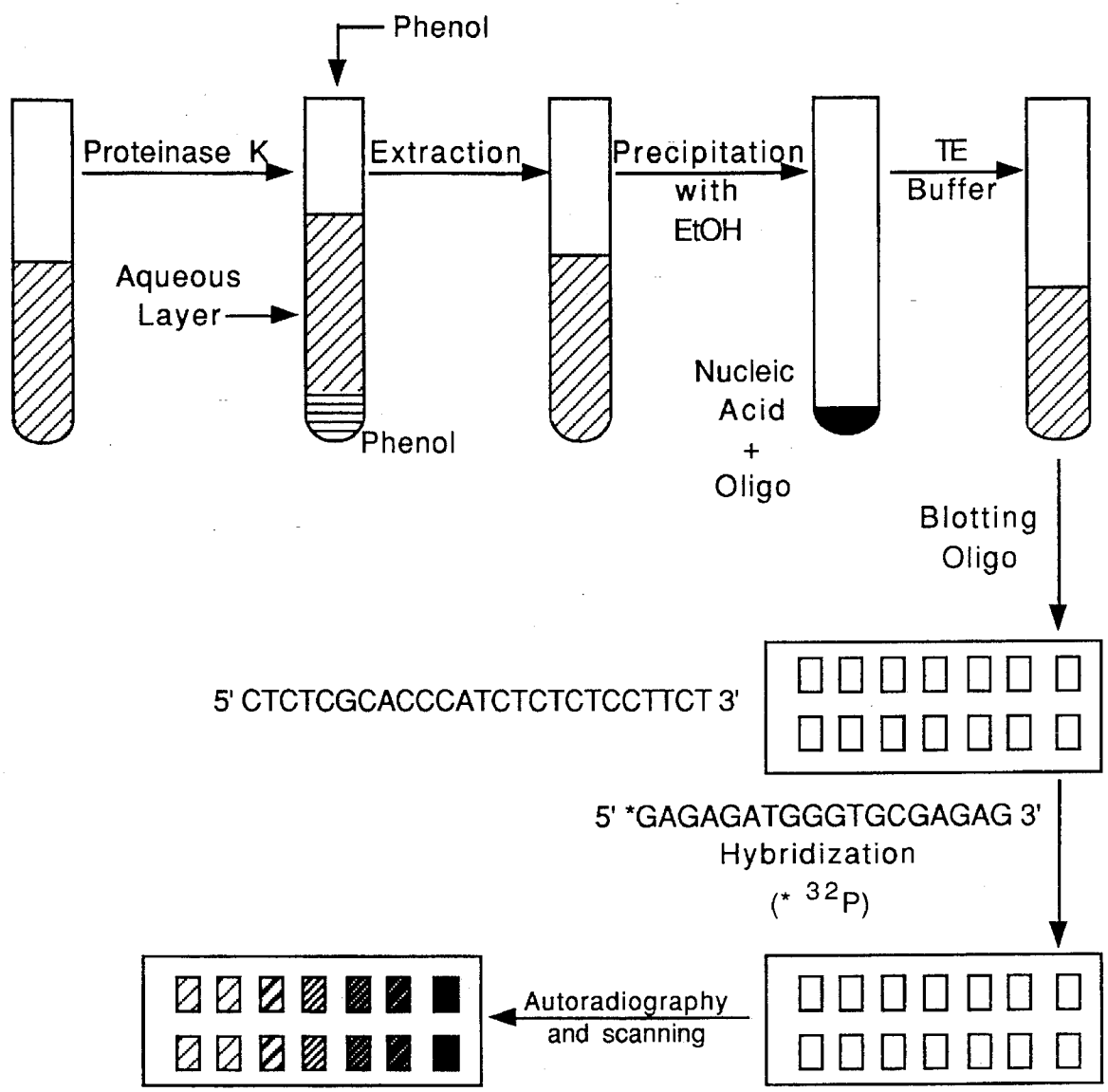
FIG. 1 is a schematic representation of an embodiment of the method according to the invention as described in detail in Examples 1–3.

The invention relates to the detection of specific nucleic acid sequences present in body fluids or tissues. In particular, the invention relates to the detection of synthetic oligonucleotides in body fluids or tissues of an animal or human patient to whom such oligonucleotides have been administered.

The invention provides a method of detecting synthetic oligonucleotides extracted from body fluids or tissues. As used herein, "oligonucleotides" include, but are not limited to, all polymers of 5' to 3' linked ribonucleosides, 2'-modified ribonucleosides and/or deoxyribonucleosides wherein the linkage may be a natural phosphodiester linkage or an artificial linkage, such as a phosphorothioate, phosphorodithioate, phosphoramidate, alkylphosphonate, akylphosphonothioate, sulfonate, carbamate or phosphotriester linkage. Moreover, such oligonucleotides encompass oligonucleotides having modifications on the bases and/or sugar residues as well as those having nuclease resistance-conferring bulky substituents at the 3' and/or 5' end. As used herein, "body fluids" include, but are not limited to, blood, urine, sweat, mucous secretions, cerebrospinal fluid and synovial fluid. "Tissues" include those constituting any organ, such as lymphoid tissue, liver, kidney, lung, brain, intestine, smooth muscle, cardiac muscle, striated muscle, dermis and epidermis, among others.

In the method according to the invention, a sample of body fluid or a tissue sample is treated in the following manner. First, the body fluid is proteolytically digested with an appropriate protease, such as proteinase K, pronase, or another conventional protease. Next, the sample is extracted with a partitioning agent, preferably with phenol/chloroform/isoamyl alcohol. Then, nucleic acids are precipitated from the sample, preferably in alcohol containing a monovalent cation, such as sodium, potassium or ammonium. Next, the nucleic acids are resuspended into solution, rendered single stranded and applied and bonded to an appropriate hybridization membrane. Such membranes include, but are not limited to, nylon and Pall A membranes. Next, the membrane having bound nucleic acids is treated with a labelled oligonucleotide that is complementary to the oligonucleotide to be detected. The complementary oligonucleotide is allowed to hybridize, then unhybridized oligonucleotide is washed away. Appropriate labels include radioisotope labels, such as $^{32}P$ or $^{35}S$, as well as any other conventional label, such as a fluorescent label like rhodamine or fluorescine, or biotin and enzymes.

Hybridization and wash conditions are especially important. For oligonucleotide phosphodiesters in 6×SSC, 16 hours of hybridization at 37° C., followed by two ten minute washes in 6×SSC at room temperature was found to be appropriate for detection of a 25-mer oligonucleotide with 56% G+C content, using a 25-mer probe having 62% G+C content. At higher stringencies, target oligonucleotide is not detected, whereas at lower stringencies background hybridization obscures true signal. For oligonucleotides having modified internucleotide linkages or lower G+C content, lower stringency (e.g., lower temperatures, higher salt concentrations) may be helpful. For longer oligonucleotides or for oligonucleotides having higher G+T content or RNA components, increases in stringency (e.g., higher temperatures, lower salt concentrations, and/or presence of hydrogen bond competitors such as formamide) may be useful. The relationship between melting temperatures and various modified internucleotide linkages has been well described (see e.g., FIG. 9 of U.S. Pat. No. 5,149,798, the teachings of which are hereby incorporated by reference). For any given modified oligonucleotide, hybridization conditions should first be worked out by starting at the conditions described in Example 3, below, using a target oligonucleotide blotted directly to the hybridization membrane. Then, stringency can be reduced or increased to account for the modifications until a limit of detection of about 1 ng target oligonucleotide is reached. It is at this level that the problems of both background and non-detection were eliminated.

Following washing, the membrane is dried and the signal is detected by conventional means, such as fluorescence detection, β-emission detection or autoradiography.

The method according to the invention is useful in animal studies of oligonucleotide pharmacokinetics, and eliminates the need to use large quantities of radiolabelled oligonucleotides in the animal. In addition, the method according to the invention is useful for detecting oligonucleotide concentration and distribution in a human patient undergoing antisense oligonucleotide therapy, thereby facilitating dosage optimization.

The following examples are intended to further illustrate certain preferred embodiments of the invention and are not limiting in nature.

EXAMPLE 1

Preparation of Body Fluid and Tissue Samples

Blood was spiked with known quantities of oligonucleotide. 500 ul of spiked blood plasma was incubated in extraction buffer (0.5% SDS/10 mM NaCl/20 mM Tris-HCl, pH 7.6/10 mM EDTA) containing 2mg/ml proteinase K for 2 hours at 37° C. The samples were then extracted once with 500 ul phenol/chloroform/isoamyl alcohol (25:24:1 vol/vol) and once with 500 µl chloroform. The aqueous phase was taken and 4M NH4OAc and 1 ml ethanol was added. After mixing, nucleic acids were precipitated and pelleted and pellets were washed with 90% ethanol and allowed to dry. Pellets were resuspended in 10 ul TE buffer (10 mM Tris-HCl, pH 8.0/1 mM EDTA) then heated to 95° C for 5 minutes. Forty ul 20×SSC (3M NaCl/0.3M sodium citrate, pH 7.0) was then added. Similar treatment can be carried out using as little as 500 µl urine or 0.5 cm³ lymphoid tissue.

EXAMPLE 2

Transfer of Extracted Nucleic Acids to a Membrane

One piece each of Nylon membrane (Zeta Probe™, Bio Rad)) and Whatman 3 MM paper were wetted in 10×SSC. Wetted Whatman paper was placed in a dot blot apparatus (Minifold II™, Schleicher & Schuell) and the wetted nylon membrane was placed atop the Whatman paper. The multiple-well lid was placed on the apparatus and latched in place, then the apparatus was hooked up to a vacuum source. Wells were rinsed with 100 µl 20×SSC, then samples prepared according to Example 1 were added in 10 µl TE+40 ml 20×SSC to the wells. Wells were then rinsed with 100 µl 20×SSC. Vacuum was then turned off and the nylon membrane removed. The nylon membrane was then exposed for 10 minutes to short wave (<300 nm) UV light at a distance of 10 cm with the topside of the membrane facing the UV source to cross-link nucleic acids to the membrane.

EXAMPLE 3

Probe Preparation, Hybridization and Signal Detection

Figure 2:
FIG. 2 shows autoradiography results obtained from the experiments described in Examples 1–3. In panel A, the control panel, 10, 1, 0.1 or 0.01 ng oligonucleotide (from top to bottom) were blotted directly to the hybridization membrane. Panel B shows identical quantities of oligonucleotides added to whole blood, then treated as described in Examples 1–3.

The membrane prepared according to Example 2 was prehybridized in 10 ml hybridization buffer (1M NaCl/1% SDS/10% dextran sulfate and 150 µg/ml tRNA) for 3 to 4 hours at 37° C. Oligonucleotide complementary to the oligonucleotide used to spike the blood, urine or tissue samples was labelled with $^{32}P$ at its 5' end in a reaction mixture containing 100 ng oligonucleotide (5 µl), 3 µl [gamma-$^{32}P$] ATP (3,000 Ci/mmole at 10 mCi/ml), 1 µl 10× kinass buffer and 1 µl T4 polynucleotide kinase (8–10 units/µl) at 37° C. for 30 minutes, then heated to 65° for 3 minutes. Labelled oligonucleotide was then precipitated with 0.4M NH$_4$OAc and ethanol and resuspended in 50 µl of H$_2$O. To the membrane in hybridization solution was added labelled oligonucleotide diluted with unlabelled complementary oligonucleotide (5×10$^5$ cpm/ml; 300 ng/ml) and incubation was continued for 16 hours at 37° C. The membrane was washed twice (10 minutes per wash) in 6×SSC, then dried at room temperature. In some experiments, the membrane was scanned with a β-scanner. In others, the membrane was exposed to x-ray film, which was then developed and subjected to scanning densitometry, with comparison to samples of known quantities of oligonucleotide that had been directly blotted to the membrane. The results, which are shown in FIG. 2 for blood samples, demonstrate detection of about 0.1 ng oligonucleotide per 0.5 ml blood. Similar results are obtained for urine and tissue samples.

We claim:

1. A method of detecting exogenous oligonucleotides present in body fluids or tissues in a concentration of at least about 0.2 ng/ml, the method comprising the steps of:

(a) proteolytically digesting a body fluid or tissue sample;

(b) extracting the proteolytically digested body fluid or tissue sample with a partitioning agent;

(c) precipitating nucleic acids present in the sample, including the exogenous oligonucleotide to be detected;

(d) resuspending the nucleic acids into a solution;

(e) binding the nucleic acids to a hybridization membrane;

(f) treating the membrane having bound nucleic acids with a labeled oligonucleotide probe that is complimentary to the exogenous oligonucleotide to be detected;

(g) washing the membrane to remove any labeled oligonucleotide that is not hybridized to nucleic acids bound to the membrane; and (h) detecting the labeled oligonucleotide being indicative of the presence of the exogenous oligonucleotide in the body fluids or tissues.

2. The method according to claim 1, wherein the body fluid is blood.

3. The method according to claim 1, wherein the body fluid is urine.

4. The method according to claim 1, wherein the tissue is lymphatic tissue.

* * * * *